United States Patent [19]

Siczek

[11] Patent Number: 5,569,266
[45] Date of Patent: Oct. 29, 1996

[54] MAGNETIC RESONANCE IMAGING DEVICE USEFUL FOR GUIDING A MEDICAL INSTRUMENT

[75] Inventor: Bernard Siczek, Boulder, Colo.

[73] Assignee: Fischer Imaging Corporation, Denver, Colo.

[21] Appl. No.: 120,744

[22] Filed: Sep. 13, 1993

Related U.S. Application Data

[63] Continuation-in-part of PCT/US93/02308 filed Mar. 12, 1993 and continuation-in-part of Ser. No. 851,683, Mar. 12, 1992, Pat. No. 5,409,497, which is a continuation-in-part of Ser. No. 667,011, Mar. 11, 1991, Pat. No. 5,129,911.

[51] Int. Cl.⁶ ..................................................... A61B 5/05
[52] U.S. Cl. .................... 606/130; 128/653.1; 128/653.5
[58] Field of Search ..................................... 606/130, 185; 604/164, 264; 128/653.1, 653.2, 653.5

[56] References Cited

U.S. PATENT DOCUMENTS

| | | | |
|---|---|---|---|
| 4,230,117 | 10/1980 | Anichkov | 128/303 |
| 4,386,602 | 6/1983 | Sheldon et al. | 128/4 |
| 4,534,358 | 8/1985 | Young | 128/653 |
| 4,543,959 | 10/1985 | Sepponen | 128/653 |
| 4,567,894 | 2/1986 | Bergman | 128/653 |
| 4,580,561 | 4/1986 | Williamson | 606/130 |
| 4,583,537 | 4/1986 | Derechinsky et al. | 128/303 |
| 4,590,947 | 5/1986 | Krause | 128/653 |
| 4,608,991 | 9/1986 | Rollwitz | 128/653.1 |
| 4,629,989 | 12/1986 | Riehl et al. | 324/318 |
| 4,722,336 | 2/1988 | Kim et al. | 128/303 |
| 4,727,565 | 2/1988 | Ericson | 378/205 |
| 4,791,934 | 12/1988 | Brunnett | 128/653 |
| 4,821,727 | 4/1989 | Levene et al. | 128/653 |
| 4,841,967 | 6/1989 | Chang et al. | 128/303 |
| 4,923,459 | 5/1990 | Nambu | 606/130 |
| 4,943,986 | 7/1990 | Barbarisi | 378/37 |
| 4,955,891 | 9/1990 | Carol | 606/130 |
| 5,003,979 | 4/1991 | Merkkel et al. | 128/653.1 |
| 5,024,229 | 6/1991 | Bryant et al. | 128/653 |
| 5,049,848 | 9/1991 | Pulyer | 335/296 |
| 5,056,523 | 10/1991 | Hotchkiss, Jr. | 606/130 X |
| 5,066,914 | 11/1991 | Vavrek et al. | 324/309 |
| 5,078,142 | 1/1992 | Siczek et al. | 128/653.1 |
| 5,125,407 | 6/1992 | Harms et al. | 128/653 |
| 5,129,911 | 7/1992 | Siczek et al. | 606/130 |
| 5,162,730 | 11/1992 | Schmitt et al. | 324/309 |
| 5,213,100 | 5/1993 | Summ | 128/653.1 |
| 5,219,351 | 6/1993 | Teubner et al. | 606/130 |

FOREIGN PATENT DOCUMENTS

| | | |
|---|---|---|
| 390653 | 10/1990 | European Pat. Off. . |
| 0483005 | 4/1992 | European Pat. Off. . |
| 861311 | 7/1941 | France . |
| 2115121 | 10/1972 | Germany ................ 606/130 |
| 2139433 | 2/1973 | Germany ................ 606/130 |
| 2239605 | 10/1991 | United Kingdom . |
| 9005492 | 5/1990 | WIPO . |

*Primary Examiner*—Angela D. Sykes
*Assistant Examiner*—Michael Peffley
*Attorney, Agent, or Firm*—Sheridan, Ross & McIntosh

[57] ABSTRACT

The disclosed system (10) employs an MRI device to identify the location of an area of interest within a patient's breast (28) and guide a medical instrument (26) for insertion to the identified location. The patient (30) is positioned on a table top (18) having an opening (52) through which the patient's breast (28) pendulantly projects. The pendulant breast (28) is immobilized by a basket (36). The table top (18) and patient (30) are then introduced into magnetic field generator (12) and MRI signals are received by receiver (14). The location of an area of interest within the patient's breast (28) is determined based on the received signals. A guidance assembly (24) can then be used to aim the medical instrument (26) towards the location of interest via a penetration path selected so as to avoid the receiver (14) and basket (36).

25 Claims, 4 Drawing Sheets

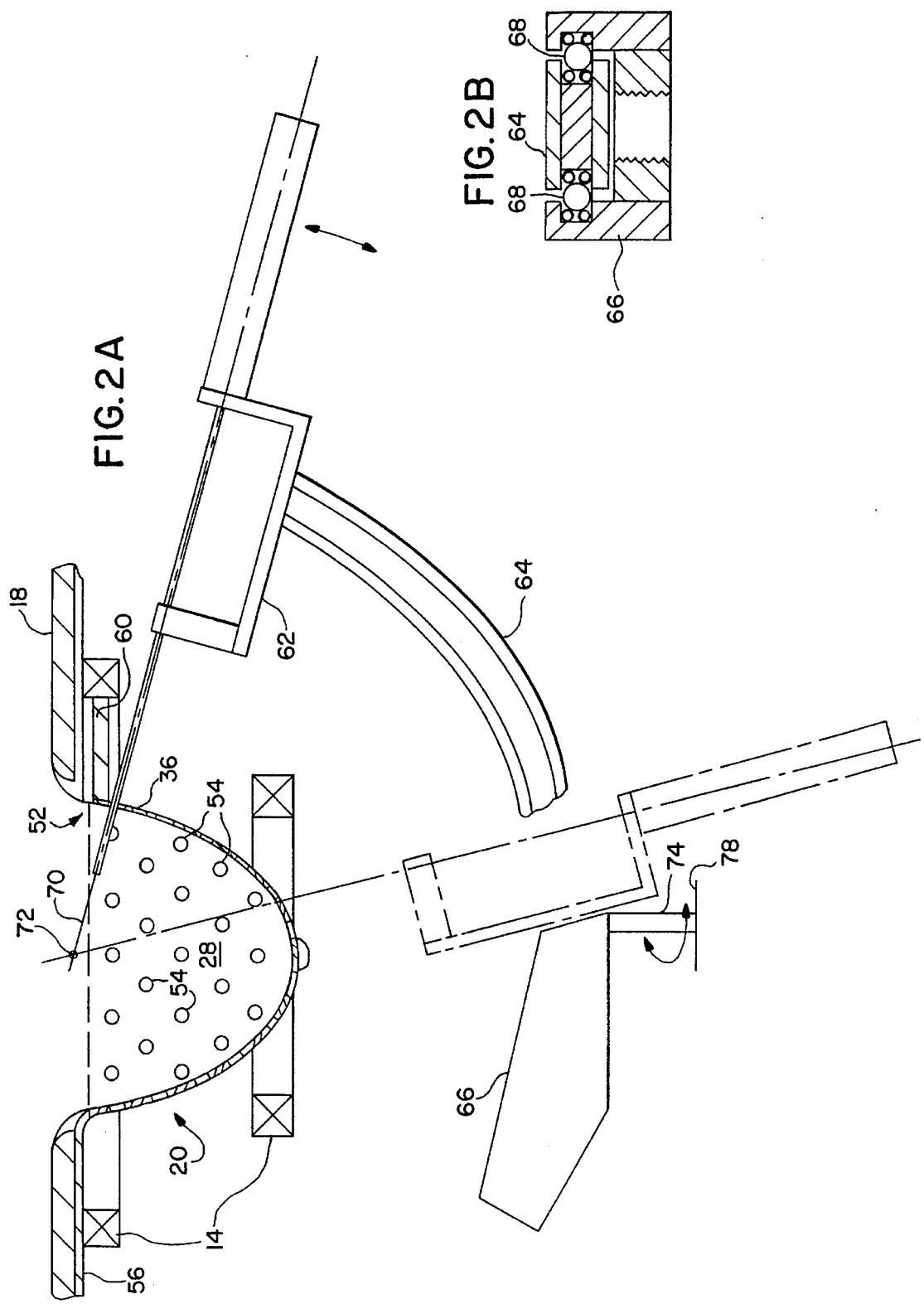

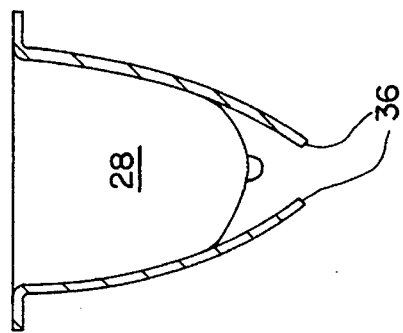
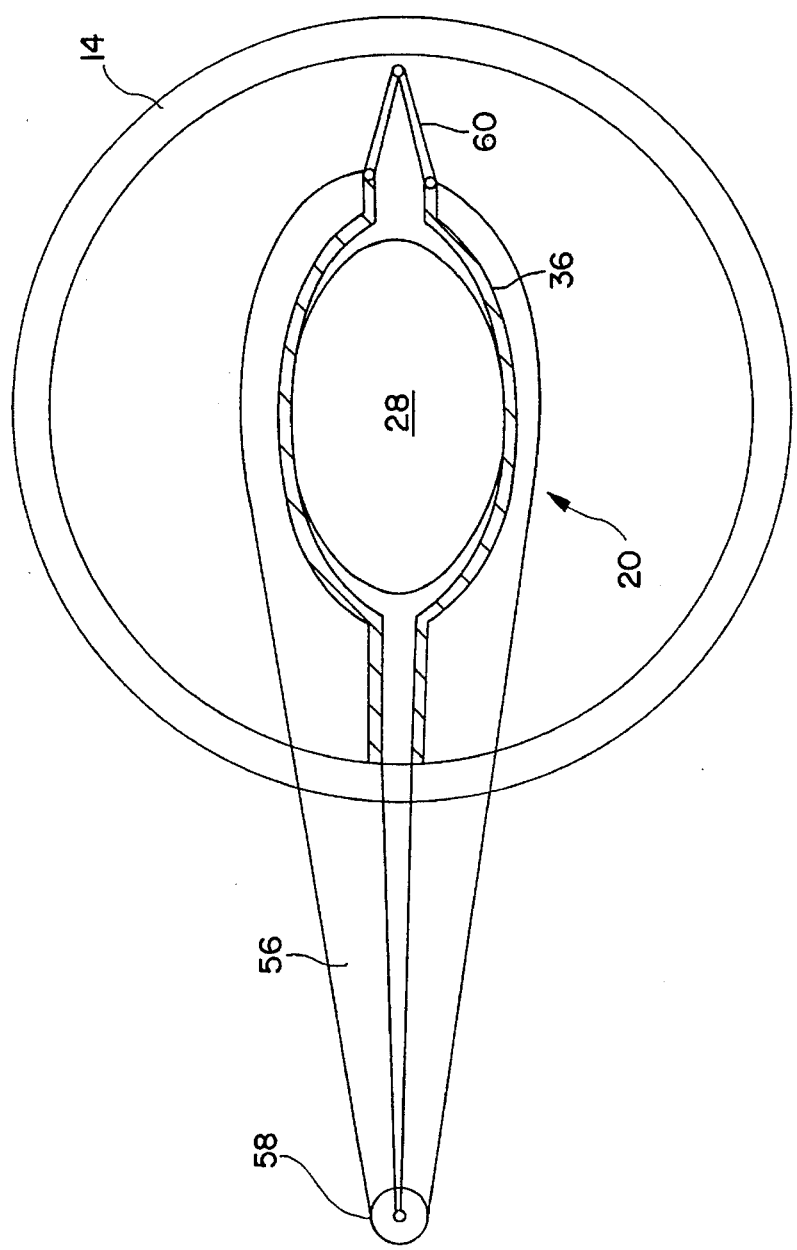

MAGNETIC RESONANCE IMAGING DEVICE USEFUL FOR GUIDING A MEDICAL INSTRUMENT

RELATED APPLICATION INFORMATION

This application is a continuation-in-part of PCT Application No. US 93/02308 filed Mar. 12, 1993 designating the United States and U.S. application Ser. No. 07/851,683, filed Mar. 12, 1992 now U.S. Pat. No. 5,409,497, which, in turn, is a continuation-in-part of U.S. application Ser. No. 7/667,011 filed Mar. 11, 1991 and now issued as U.S. Pat. No. 5,129,911. PCT Application No. US 93/02308, U.S. Pat. No. 5,409,497 and U.S. Pat. No. 5,129,911 are incorporated herein by reference in their entireties.

FIELD OF THE INVENTION

This invention relates generally to breast imaging and, in particular, to a device which employs magnetic resonance imaging for locating an area of interest within a patient's breast and which is also useful for guiding a medical instrument to the area of interest. The device is particularly useful for sampling, excising or treating breast lesions including lesions suspected of being cancerous.

BACKGROUND OF THE INVENTION

X-ray mammography has long been considered the "gold standard" of breast imaging and is well-developed and capable of yielding outstanding image resolution. In x-ray mammography, x-rays are transmitted through the patient's breast and impinge upon x-ray film or a digital imaging camera. Internal features of the patient's breast are depicted as shadows in the resulting image due to differences in x-ray absorption between differing types of tissue. Ordinarily, the patient's breast is compressed during x-ray mammography so that the breast is of more uniform thickness, thereby enhancing the resulting image. In addition to pure imaging applications such as patient screening or diagnosis, x-ray mammography has been used to localize breast lesions for needle biopsy or for placement of a wire or markings to guide a surgeon during subsequent surgical biopsy.

Recently, magnetic resonance imaging (MRI) has been investigated for use in breast imaging. Generally, in MRI, atomic nuclei which possess nuclear magnetic momentum, or spin, are first aligned in a relatively strong magnetic field and are then excited by radio frequency (RF) resonance energy. When their spin returns to equilibrium they emit energy in the form of an RF signal. The time of emission of the absorbed energy, called the relaxation time, depends on magnetic properties of the tissue. The emitted signal can be analyzed to obtain imaging information regarding the tissue under examination. Ordinarily, specified regions or slices of the tissue are sequentially examined so that a composite image of the tissue under examination is obtained.

MRI is of interest to breast imaging specialists for various reasons. Initially, MRI avoids cumulative radiation exposure, a concern expressed by some in connection with alternative x-ray imaging techniques. Additionally, MRI reduces the need to compress the patient's breast to a uniform thickness, thereby potentially enhancing patient comfort. Moreover, MRI may provide imaging advantages for certain soft tissue imaging applications due to its reliance on nuclear magnetic relaxation times rather than x-ray absorption or other characteristics. Advances in MRI technology are also improving MRI resolution.

However, as to breast imaging, a number of challenges remain in realizing the full potential of MRI. For example, conventional tunnel MRI devices where a patient is axially positioned within a magnetic tunnel are intended for obtaining a composite image from axial body slices. These systems are not tailored for breast imaging and, standing alone, are not capable of yielding the images necessary for increasingly acute breast diagnostic techniques.

Moreover, known MRI devices are not adapted for use in localizing a breast lesion so as to permit insertion of a medical instrument to sample, excise or treat the lesion. With regard to conventional tunnel MRI devices, due to space limitations within the tunnel bore, it is impractical to perform procedures involving insertion of a medical instrument into a patient's breast while the patient remains in an imaging position within the bore. In addition, such devices do not provide a mechanism for allowing localization of a breast lesion after the patient has been withdrawn from the tunnel bore. Known MRI devices which are dedicated to breast imaging generally include magnetic generators and signal transmitters/receivers which surround the patient's breast. These components can interfere with conventional medical instrument insertion devices.

SUMMARY OF THE INVENTION

The present invention provides an MRI device generally useful for imaging a patient's breast, and particularly apt for localizing an area of interest within the patient's breast and readily and accurately obtaining a sample therefrom by insertion of a medical instrument. The invention can advantageously utilize elements of a conventional tunnel MRI device, as is often available on premises, thereby simplifying device construction. Additionally, the device provides for breast specific MRI without interfering with medical device insertion.

According to one aspect of the invention, an MRI/guidance device includes a breast imaging assembly comprising an MRI signal receiver, such as a coil for receiving radio frequency signals, which is dimensioned to receive the breast under examination. The receiver coil can also be utilized, in cooperation with a magnetic field generator for producing a local magnetic field, to transmit an MRI signal.

Alternatively, the transmitted MRI signal, or just the magnetic field employed in transmitting the signal, can be provided by a conventional tunnel MRI device. In one embodiment, a specialized table is provided for supporting the patient and a signal receiver and for permitting the patient and receiver to be introduced into the bore of a conventional tunnel MRI device. The table supports the patient in a prone position and includes an opening through which the patient's breast is permitted to pendulantly protrude. The receiver is supported by the table such that the receiver surrounds the patient's pendulant breast. In this manner, elements of a conventional tunnel MRI device can be utilized while obtaining the advantages of a localized receiver. The table is moveable between an extended position where the patient's breast is centrally disposed within the bore of the MRI tunnel and a retracted position where the patient is withdrawn from the bore. A mechanism such as bumpers, detents or the like is utilized to ensure accurate registration of the table in the extended and retracted positions.

According to another aspect of the invention, the MRI/guidance device includes an assembly for immobilizing the patient's breast such that information obtained via MRI can subsequently be used for identifying an area of interest within the patient's breast and for inserting a medical instrument to the identified area of interest. The patient's breast is immobilized by a contractible basket which engages the patient's breast. The basket is disposed between the signal receiver and the patient's breast. Preferably, the basket is shaped to generally conform to the contours of the patient's breast and includes a number of openings to allow for insertion of a medical instrument therethrough. In one embodiment, the basket is formed in two halves which are interconnected using a spring or other resilient member so that the halves are drawn towards a contracted position to engage the patient's breast.

According to a further aspect of the present invention, the MRI/guidance device includes a medical instrument guidance assembly for aiming a medical instrument to an identified area of interest within the patient's breast. Based on MRI information, the guidance assembly directs a medical instrument towards the area of interest via a penetration path which avoids obstructions such as the signal receiver and/or breast immobilization assembly.

In this regard, the guidance assembly supports the medical instrument so that the medical instrument is moveable between at least a first position and a second position wherein the medical instrument is aimed at a common point, the isocenter, in each of the first and second positions. For example, the medical instrument can be orbitally moved relative to the isocenter so that the medical instrument pivots thereabout in a single plane (defined by movement of the aiming axis) and/or the medical instrument can be rotationally moved relative to the isocenter so that the puncture instrument pivots thereabout in three-dimensions. Aiming the medical device at the area of interest is accomplished by moving the patient and/or guidance assembly so that the area of interest coincides with the isocenter. The medical instrument can then be inserted to the area of interest for sampling, excision or treatment as desired.

The present invention thus allows for use of a conventional tunnel MRI device while obtaining the advantages of localized, breast specific signal reception. The invention also allows for insertion of a medical instrument to an identified area of interest within the patient's breast, e.g., a breast lesion, under MRI guidance. Further advantages of the present invention will be appreciated upon consideration of the Detailed Description below taken in conjunction with the Drawings.

BRIEF DESCRIPTION OF THE DRAWINGS

FIG. 2a is a side view of the medical instrument guidance assembly which forms a portion of the device of FIG. 1;

FIG. 2b is a cross-sectional view of the medical instrument guidance assembly of FIG. 2a illustrating the slidable interconnection which facilitates orbital movement of the medical instrument;

FIG. 3b is a bottom view showing the breast immobilization basket assembly; and

FIG. 3c is a front view of the breast immobilization basket.

DETAILED DESCRIPTION

Figure 1:
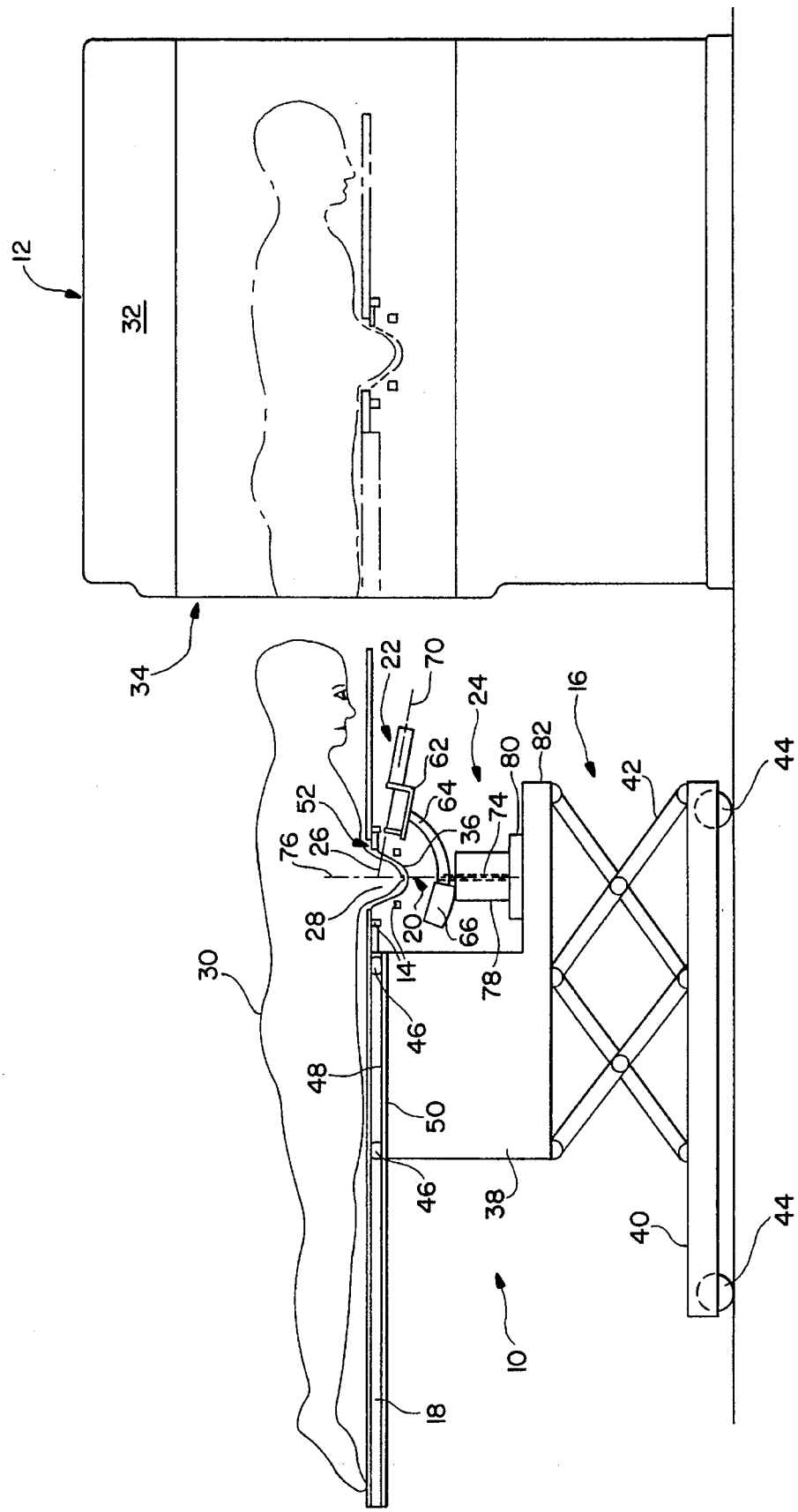
FIG. 1 is a side view of a MRI/guidance device constructed in accordance with the present invention.

Referring to FIGS. 1–3c, an MRI/guidance system is generally identified by the reference numeral 10. The system 10 comprises a magnetic field generator 12, a signal receiver 14, a stretcher assembly 16 including an extendible table top 18, a breast immobilization basket assembly 20, a medical instrument insertion assembly 22, and a guidance assembly 24 for aiming a medical instrument 26.

The system 10 employs known MRI principles to image a breast 28 of a patient 30. As is known, MRI generally involves subjecting the tissue to be imaged to a strong magnetic field, applying an RF signal to the tissue and receiving an RF signal from the tissue. In accordance with the present invention, the magnetic field may be specifically directed to the breast under examination via a dedicated magnetic field generator or the less localized magnetic field of a tunnel MRI device may be utilized.

In the illustrated embodiment, the magnetic field generator 12 comprises a conventional tunnel MRI device as is commonly available at medical imaging facilities, thereby eliminating the need for a magnetic field generator dedicated to breast imaging applications. The generator 12 comprises a resistive or superconductive magnet 32 which is generally configured in the shape of a cylinder. The illustrated generator can further include a shim coil to correct magnet field inhomogeneities and a gradient coil for producing a magnetic field gradient for encoding spatial information into the imaging signals. In addition, conventional tunnel MRI systems normally include a body coil for applying an RF signal to the patient 30. As will be described below, this RF signal can alternatively be applied in accordance with the present invention via receiver 14. These components are disposed about a central bore 34 of sufficient size to receive the patient 30 therein. The generator 12 may comprise, for example, the SIGMA system manufactured by General Electric.

Stretcher assembly 16 is utilized for transporting the patient 30 into and out of bore 34. The stretcher assembly 16 comprises an extendible table top 18 supported by platform 38. Platform 38, in turn, is supported on base 40 via collapsible platform jack 42 so as to allow for adjustment of the height of table top 18. In this regard, the height of table top 18 is preferably adjusted so that the breast 28 under examination is centrally disposed within bore 34 for optimal imaging. Conveniently, assembly 16 can be provided with rollers to facilitate positioning of assembly 16 relative to generator 12.

Table top 18 is axially moveable relative to bore 34 between an extended position wherein the patient 30 is disposed within bore 34 for imaging (shown in phantom in FIG. 1) and a retracted position for performing further medical procedures on the patient's breast 28. To facilitate movement of table top 18, rollers 46 are provided on upper surface 48 of platform 38. The rollers 46 roll in tracks formed in lower surface 50 of table top 18 to ensure that movement of table top 18 is aligned axially with bore 34. The rollers 46 and the tracks of table top 18 should be formed from non-magnetic materials such as stainless steel to provide for smooth rolling movement of table top 18. It will be appreciated that, in the illustrated system 10, all components utilized in close proximity to magnetic generator 12 are formed from materials which do not affect the homogeneity of the magnetic field used. To obtain good images, the magnetic field has to be homogeneous to a very high degree.

As will be understood upon consideration of the description below, it is useful to provide for positive registration of the table top 18 in the extended and retracted positions. In this regard, bumpers can be provided on the upper surface 48 of platform 38 and/or lower surface 50 of table top 18 to positively limit table top movement. Alternatively, a detent may be provided on one of these surfaces or elsewhere to accurately control the relative positioning of table top 18 and platform 38.

As shown, the patient 30 lies in a prone position on table top 18. At least one opening 52 is provided in table top 18 to allow the breast 28 under examination to pendulantly protrude through the table top 18. The illustrated table top includes two openings 52 positioned so that either of the patient's breasts can be examined. This pendulant positioning of the patient's breast 28 is advantageous in that the breast 28 is drawn downwardly by gravity, thereby facilitating access to areas of interest within the patient's breast 28 near the chest wall.

The receiver 14 and basket assembly 20 for immobilizing the patient's breast 28 also travel with table top 18 so that a fixed spatial relationship is maintained. As noted above, the receiver 14 is disposed in close proximity to the breast 28 under examination and surrounds the breast 28 so as to provide high resolution, breast specific signal reception. In this regard, the illustrated receiver 14 comprises an RF receiver coil provided in a generally conical configuration. The receiver 14, together with the basket assembly 20, as will be described below, is connected to table top 18 so that the receiver surrounds opening 52 in table top 18 to receive the patient's breast 28. In addition, the receiver 14 communicates with a conventional MRI signal processing unit, which can comprise a digital computer, for acquiring data and reconstructing images based on the received signals. The receiver coils can also be utilized to transmit the RF signal which cooperates with the magnetic field to provide the MRI signal.

Basket assembly 20 is interposed between receiver 14 and the patient's breast 28. The basket assembly 20 immobilizes the patient's breast 28 relative to table top 18 so that localization information derived in the MRI procedure can be used in guiding the medical instrument 26 to an area of interest within the patient's breast 28. Accordingly, the basket assembly 20 is connected to table top 18 to receive the breast 28 protruding through opening 52.

Figure 3A:
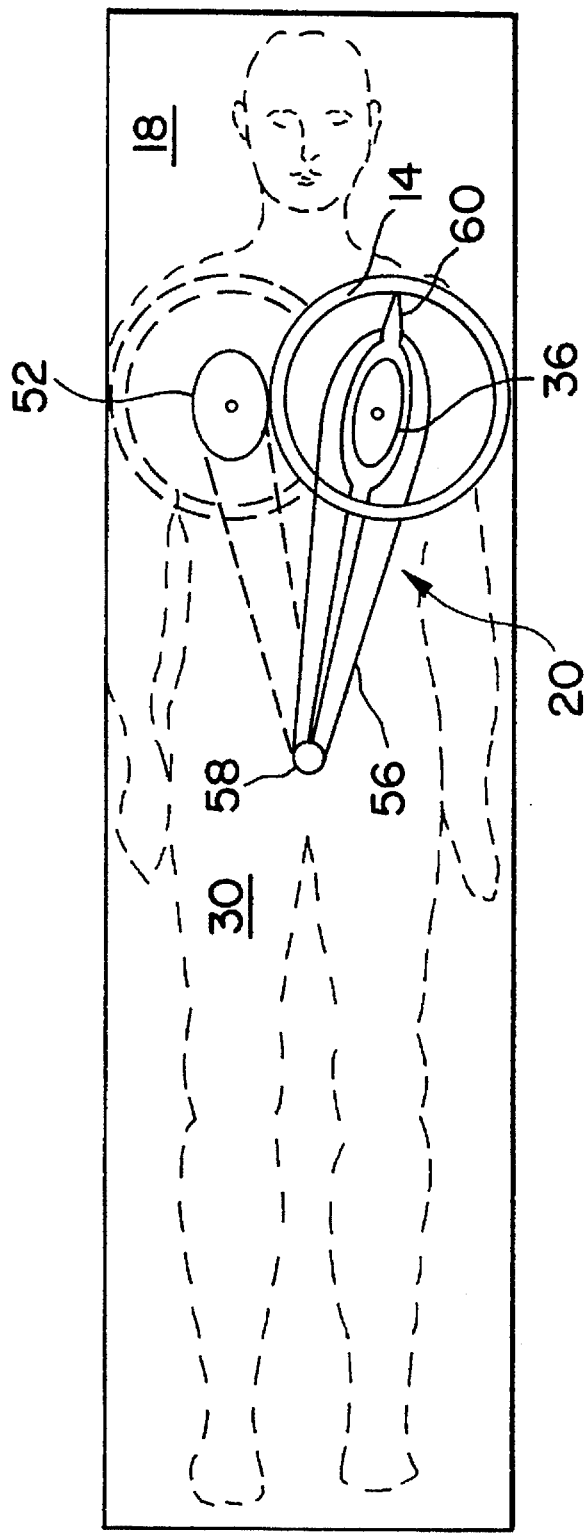
FIG. 3a is a bottom view of the device of FIG. 1 illustrating a technique for positioning the breast immobilization basket and signal receiver coil relative to the patient.

As shown most clearly in FIG. 3a, the basket assembly 20 comprises a basket 36 formed in two halves which are drawn together to engage the patient's breast 28. The basket 36 is shaped to generally conform to the contours of the patient's breast 28 thereby enhancing patient comfort. It will be appreciated that it is unnecessary in MRI to compress the breast 28 to a uniform thickness. In addition, the basket 36 includes a number of openings 54 of any suitable shape to allow insertion of the medical instrument 26 therethrough. Additional baskets 36 of various sizes can be provided for interconnection to table top 18 to accommodate patients of different sizes. The basket 36 is formed from a material such as one of various plastics which does not unduly interfere with the MRI procedure.

The two halves of basket 36 are connected via arms 56 to a common non-magnetic hinge 58 and are drawn together by a non-magnetic spring loaded connection 60. Receiver 14 is also mounted to table top 18 via hinge 58 so as to move with basket 36. The hinge 58 is positioned such that the basket 36 and receiver 14 can be moved across the patient's chest from one breast to the other. In this manner, table top 18 can be utilized to perform medical procedures on either breast without awkwardly positioning the patient 30 on table top 18.

The medical instrument insertion assembly 22 is used to insert a medical instrument 26 to an area of interest within the patient's breast 28 identified through MRI. The nature of the medical instrument 26 and insertion assembly 22 depends on the particular procedure to be performed. One such procedure is a needle biopsy to obtain a cell or tissue sample from a suspicious lesion for diagnosing the nature of the lesion, e.g., cancerous, benign, or more specifically, fibroadenoma, ductile carcinoma, etc. Other procedures which can be conducted using the system 10 include various trans-cannula procedures such as cryoablation, laser ablation, hyperthermia, medicament delivery, percutaneous removal, draining or other procedures for treating or eliminating a lesion, cyst or other area of interest. Thus, the insertion assembly 22 can simply be a guide for facilitating manual insertion of a biopsy needle, trocar and cannula, or other instrument, or the assembly can be a mechanized delivery system. In the illustrated embodiment, insertion assembly 22 comprises a biopsy gun for rapid delivery of a biopsy needle to an identified lesion.

The guidance assembly 24 is used for aiming the medical instrument 26 at the identified area of interest within the patient's breast 28 and allows for selection of a penetration path wherein the receiver 14 and basket 36 are avoided. Accordingly, the guidance assembly 24 allows the medical instrument 26 to pass between the coils of receiver 14 and through an opening 54 of basket 36 en route to the area of interest. The guidance assembly 24 comprises a platform 62 for supporting the medical instrument insertion assembly 22. The platform 62 is mounted on an arcuate rail 64 which is slidably received within housing 66 via bearings 68 (FIG. 2b). In this manner, the insertion assembly 22 can be orbitally moved by sliding rail 64 within housing 66, as shown in phantom in FIG. 2a, such that the aiming axis 70 of medical instrument 26 remains directed at isocenter 72.

In addition, the insertion assembly 22 can be rotationally moved around the patient's breast 28 while the aiming axis 70 of medical instrument 26 remains directed at isocenter 72. Housing 66 is thus mounted on shaft 74 for rotation about shaft axis 76. The intersection of the aiming axis 70 and shaft axis 76 thus defines the isocenter 72. It will thus be appreciated that the combination of orbital and rotational movement of the medical instrument 26 allows for variation of the penetration path of the medical instrument 26 with respect to breast approach angle and with respect to inclination angle relative to the chest wall.

Targeting of an area of interest within the patient's breast is accomplished by positioning the patient 30 and/or the guidance assembly 24 so that the area of interest coincides with the isocenter 72 of guidance assembly 24. In the illustrated embodiment, guidance assembly 24 is moveable relative to stretcher assembly 16 and patient 30. To adjust the height of guidance assembly 24, shaft 74 can be raised or lowered within cylinder 78 mounted on base 80. Base 80 is slidably moveable on recessed surface 78 of platform 38 so that guidance assembly 24 can be moved side-to-side or forward-to-rearward relative to the patient's chest. For example, cylinder 78 can be mounted for forward-to-rearward movement relative to base 80, and base 80 can be mounted for side-to-side movement relative to surface 82. Appropriate brakes may be provided between all moveable components of guidance assembly 24 to lock the assembly into a selected position.

In order to allow for accurate targeting of an area of interest within the patient's breast 28, the spatial relationship between the area of interest and guidance assembly 24 must be known. This can be accomplished by providing at least one reference marker which appears in the images used for localizing the area of interest and which has a known location relative to the guidance assembly 24 when the system 10 is configured for medical device insertion. In the illustrated embodiment, this purpose is served by incorporating three high contrast markers into, or attaching three high contrast markers to the basket 36. The markers may comprise oil capsules and/or may include gadolinium or other contrast materials.

Any of the above-described movements of system can be motorized if desired. However, care must be taken to ensure that such motors do not interfere with and are otherwise compatible with the magnetic field generator 12. In this regard, hydraulic motors may be disposed in a separate, shielded room where the necessary power is transmitted to the appropriate components of system 10 by hydraulic lines.

In summary, the system 10 operates as follows. The stretcher assembly is first positioned adjacent the magnetic field generator 12 and the height of the table top 18 is adjusted relative to the bore 34 of generator 12. The table top 18 is then extended so that the patient 30 is centrally disposed within bore 34. Receiver 14 is utilized in combination with generator 12 to transmit MRI signals and is also used to receive signals from the tissue under examination. MRI images of the patient's breast 28 are thus obtained. Based on these images, the location of an area of interest within the patient's breast 28 is determined. With the table top 18 in the retracted position, the guidance assembly 24 is positioned so that the isocenter 72 thereof coincides with the identified area of interest. The guidance assembly can then be manipulated to select a penetration path for medical instrument 26 wherein interference with the receiver 24 and basket 36 is avoided.

While various embodiments of the present invention have been described in detail, it is apparent that further modifications and adaptations of the invention will occur to those skilled in the art. However, it is to be expressly understood that such modifications and adaptations are within the spirit and scope of the present invention.

What is claimed is:

1. An apparatus for use in performing medical procedures on a patient's breast, comprising:

an immobilizer for immobilizing said patient's breast within a predetermined frame of reference;

magnetic resonance imaging means, disposed relative to said patient's immobilized breast for imaging said patient's breast including transmitting means for applying a signal to said patient's breast and receiving means for receiving a signal from said patient's breast, said magnetic resonance imaging means defining a volume dimensioned for receiving said patient's breast and accommodating said immobilizer so as to provide breast specific magnetic resonance imaging information, said immobilizer means disposed at least partially between said patient's breast and said receiving means;

identifying means, interconnected to said magnetic resonance imaging means so as to receive said imaging information, for identifying the location of an area of interest within said patient's breast based on said breast specific magnetic resonance information; and a medical instrument positioner, disposed in predetermined relation to and moveable relative to said predetermined frame of reference, for use in selectively targeting a medical instrument to said identified location of said area of interest within said patient's breast via a penetration path wherein said immobilizer and said magnetic resonance imaging means are avoided, whereby said breast specific magnetic resonance imaging information is employed for instrument guidance substantially without penetration path interference.

2. The apparatus of claim 1, wherein said magnetic resonance imaging means comprises cylindrical magnetic means for receiving said patient therein.

3. The apparatus of claim 1, wherein said medical instrument positioner comprises penetration path selection means for selecting a penetration path for inserting said medical instrument to said identified location of said area of interest within said patient's breast wherein the location of at least one of said immobilizer and said receiving means is accounted for in selecting said penetration path.

4. The apparatus of claim 1, wherein said medical instrument positioner comprises isocentric support means adapted to movably support said medical instrument so that said medical instrument is moveable between a first position and a second position wherein said medical instrument is aimed at an isocenter of said support means in each of said first and second positions.

5. The apparatus of claim 1, further comprising a biopsy gun, carried by said medical instrument positioner, for rapid insertion of a biopsy needle to said identified location of said area of interest within said patient's breast.

6. The apparatus of claim 1, further comprising table means for supporting said patient in a prone position, said table means having an opening therein through which said patient's breast is permitted to pendulantly protrude within said predetermined frame of reference.

7. The apparatus of claim 6, further comprising table positioning means for moving said table means between a first position wherein said patient's breast is positioned for imaging and a second position wherein said patient's breast is positioned for insertion of said medical instrument.

8. An apparatus for use in performing medical procedures on a patient's breast, comprising:

an immobilizer for immobilizing said patient's breast within a predetermined frame of reference, said immobilizer comprising a contractible member shaped to generally conform to the contour's of said patient's breast;

magnetic resonance imaging means, adapted for receiving said patient's immobilized breast in an imaging position relative thereto, for imaging said patient's breast including transmitting means for applying a signal to said patient's breast and receiving means for receiving a signal from said patient's breast, said magnetic resonance imaging means defining a volume dimensioned for receiving said patient's breast and accommodating said immobilizer, wherein said magnetic resonance imaging means provides imaging information regarding said patient's breast;

identifying means, interconnected to said magnetic resonance imaging means so as to receive said imaging information, for identifying the location of an area of interest within said patient's breast; and a medical instrument positioner, disposed in predetermined relation to and moveable relative to said predetermined frame of reference, adapted to selectively insert a medical instrument to said identified location of said area of interest within said patient's breast via a penetration path wherein said immobilizer and said magnetic resonance imaging means are avoided.

9. The apparatus of claim 8, wherein said contractible member comprises a basket formed in two halves which are urged together by a resilient member.

10. An apparatus for use in performing medical procedures on a patient's breast, comprising:

an immobilizer for immobilizing said patient's breast within a predetermined frame of reference;

magnetic resonance imaging means, adapted for receiving said patient's immobilized breast in an imaging position relative thereto, for imaging said patient's breast including transmitting means for applying a signal to said patient's breast and receiving means for receiving a signal from said patient's breast, said magnetic resonance imaging means defining a volume dimensioned for receiving said patient's breast and accommodating said immobilizer, wherein said magnetic resonance imaging means provides imaging information regarding said patient's breast;

reference mark means, disposed in predetermined relation to said predetermined frame of reference, for providing reference marks useful for analyzing images of said patient's breast, said reference mark means comprising a contrast material disposed in predetermined spatial location relative to said predetermined frame of reference;

identifying means, interconnected to said magnetic resonance imaging means so as to receive said imaging information, for identifying the location of an area of interest within said patient's breast; and a medical instrument positioner, disposed in predetermined relation to and moveable relative to said predetermined frame of reference, adapted to selectively insert a medical instrument to said identified location of said area of interest within said patient's breast via a penetration path wherein said immobilizer and said magnetic resonance imaging means are avoided.

11. An apparatus for use in performing medical procedures on a patient's breast, comprising:

an immobilizer for immobilizing said patient's breast within a predetermined frame of reference;

magnetic resonance imaging means, adapted for receiving said patient's immobilized breast in an imaging position relative thereto, for imaging said patient's breast using a magnetic resonance imaging signal and providing imaging information regarding said patient's breast;

identifying means, interconnected to said magnetic resonance imaging means so as to receive said imaging information for identifying the location of an area of interest within said patient's breast;

a medical instrument targeting assembly, disposed in predetermined relation to and moveable relative to said predetermined frame of reference, adapted to target a medical instrument to said identified location of said area of interest within said patient's breast;

said medical instrument targeting assembly including penetration path selection means adapted to provide a range of penetration paths for inserting a medical instrument to a target point of said medical instrument targeting assembly; and positioning means for positioning said medical instrument targeting assembly relative to said predetermined frame of reference such that said target point of said instrument targeting assembly coincides with said identified area of interest and said range of penetration paths of said penetration path selection means includes at least a first penetration path for inserting a medical instrument to said location of said area of interest which is intersected by one of said immobilizer and said magnetic resonance imaging means and a second penetration path for inserting a medical instrument to said identified location of said area of interest which is free from interference by said immobilizer and said magnetic resonance imaging means, wherein a location of at least one of said immobilizer and said magnetic resonance imaging means is accounted for in selecting a penetration path for inserting a medical instrument to said identified location of said area of interest within said patient's breast.

12. The apparatus of claim 11, wherein said penetration path selection means comprises isocentric support means adapted to movably support said medical instrument so that said medical instrument is moveable between a first position and a second position wherein said medical instrument is aimed at an isocenter of said support means in each of said first and second positions.

13. The apparatus of claim 12, wherein said support means is adapted to orbitally move said medical instrument across said range of positions relative to said isocenter, said range of positions defining a substantially planar region.

14. The apparatus of claim 12, wherein said support means is adapted to rotationally move said puncture instrument across said range of positions relative to said isocenter, said range of positions defining a three-dimensional region.

15. The apparatus of claim 11, further comprising table means for supporting said patient in a prone position, said table means having an opening therein through which said patient's breast is permitted to pendulantly protrude within said predetermined frame of reference.

16. An apparatus for use in performing medical procedures on a patient's breast, comprising:

table means for supporting said patient in a prone position, said table means having an opening therein through which said patient's breast is permitted to pendulantly protrude within a predetermined frame of reference;

an immobilizer, positionable relative to said opening of said table means for immobilizing said patient's breast in a fixed position with respect to said predetermined frame of reference;

magnetic resonance imaging means, adapted for receiving said patient's immobilized breast in an imaging position relative thereto, for imaging said patient's breast, said magnetic resonance imaging means including a generally cylindrical component defining an internal axial bore; and positioning means for axially moving said table means relative to said bore between a first position wherein said patient is disposed at a first predetermined location within said bore for imaging said patient's breast and a second position wherein said patient is disposed at a second predetermined location outside said bore, wherein said patient's breast is maintained in said same fixed position with respect to said predetermined frame of reference when said table means is in said first position and when said table means is in said second position such that imaging information obtained in said first position can be correlated to a location of said patient's breast in said second position.

17. The apparatus of claim 16, wherein said immobilizer comprising a contractible member shaped to generally conform to the contours of said patient's breast.

18. The apparatus of claim 16, wherein said immobilizer comprising a basket formed in two halves which are urged together by a resilient member.

19. The apparatus of claim 16, wherein said immobilizer means is interconnected to said table means so as to allow for movement of said immobilizing means across said patient's chest.

20. An apparatus for use in performing medical procedures on a patient's breast, comprising:

table means for supporting said patient in a prone position, said table means having an opening therein through which said patient's breast is permitted to pendulantly protrude within a predetermined frame of reference;

magnetic resonance imaging means for imaging said patient's breast including transmitting means for transmitting a first signal to said patient's breast, magnetic means for producing a magnetic field, said magnetic means including a generally cylindrical component defining an internal axial bore for receiving said table means therein, and receiving means, disposed in predetermined relation to said predetermined frame of reference, for receiving a second signal from said patient's breast, said receiving means defining a volume dimensioned for receiving said patient's pendulant breast so as to provide breast specific magnetic resonance imaging information; and positioning means for axially moving said table means relative to said bore between a first position wherein said patient is disposed within said bore for imaging said patient's breast and a second position wherein said patient is disposed outside said bore.

21. The apparatus of claim 20, wherein said receiving means is interconnected to said table means so as to allow for movement of said receiving means across said patient's chest.

22. The apparatus of claim 20, wherein said axial bore has a top, a bottom, and a center located mid-way between said top and bottom, and said positioning means positions said table means at said first position such that said table means is located at a height near to the height of said center.

23. An apparatus for use in inserting a medical instrument to an area of interest within a patient's body, comprising:

a patient support for supporting a patient in a fixed position relative to a predetermined frame of reference;

magnetic resonance imaging means, disposed at a first location and adapted for receiving said patient support, for imaging said area of interest within said patient's body, said magnetic resonance imaging means including transmitting means for transmitting an imaging signal to said patient's body and receiving means for receiving an imaging signal from said patient's body, wherein said magnetic resonance imaging means provides localization information regarding a location of said area of interest within said patient's body;

medical instrument support means, disposed at a second location separate from said first location and positionable relative to said predetermined frame of reference, for supporting a medical instrument such that said medical instrument can be inserted into said patient's body; and targeting means disposed in predetermined relation to and moveable relative to said predetermined frame of reference, for use in targeting said medical instrument at said area of interest within said patient's body using only said localization information provided by said magnetic resonance imaging means.

24. The apparatus of claim 23, further comprising positioning means, operatively associated with said patient support, for moving said patient support between said first location for imaging said area of interest and said second location for inserting said medical instrument into said patient's body, wherein said patient is maintained in said same fixed position relative to said predetermined frame of reference in said first and second locations.

25. The apparatus of claim 24, wherein said positioning means comprises first docking means for providing an indication that said patient support is positioned at said first location for imaging said area of interest and second docking means for providing an indication that said patient support is at said second location for inserting said medical instrument into said patient's body.

* * * * *